(12) United States Patent
Hodson

(10) Patent No.: US 7,497,214 B2
(45) Date of Patent: Mar. 3, 2009

(54) AEROSOL DISPENSERS AND ADAPTORS THEREFOR

(75) Inventor: Peter D. Hodson, Breaston (GB)

(73) Assignee: 3M Innovative Properties Company, St. Paul, MN (US)

( * ) Notice: Subject to any disclaimer, the term of this patent is extended or adjusted under 35 U.S.C. 154(b) by 480 days.

(21) Appl. No.: 10/525,918

(22) PCT Filed: Aug. 13, 2003

(86) PCT No.: PCT/US03/25502

§ 371 (c)(1),
(2), (4) Date: Feb. 25, 2005

(87) PCT Pub. No.: WO2004/024221

PCT Pub. Date: Mar. 25, 2004

(65) Prior Publication Data

US 2006/0011197 A1    Jan. 19, 2006

(30) Foreign Application Priority Data

Sep. 16, 2002  (GB)  ................................ 0221343.7

(51) Int. Cl.
*A61M 11/00* (2006.01)
(52) U.S. Cl. ................ 128/200.23; 222/402.2
(58) Field of Classification Search ........... 128/200.23, 128/200.14, 204.23, 204.21, 203.15; 239/338; 222/402.2, 162
See application file for complete search history.

(56) References Cited

U.S. PATENT DOCUMENTS

| 2,980,301 | A |   | 4/1961  | Gorter |
|-----------|---|---|---------|--------|
| 3,157,179 | A |   | 11/1964 | Paullus et al. |
| 3,176,887 | A |   | 4/1965  | Potapenko et al. |
| 3,176,889 | A |   | 4/1965  | Potapenko et al. |
| 3,591,059 | A |   | 7/1971  | Stearns |
| 4,506,803 | A |   | 3/1985  | Franklin et al. |
| 4,648,393 | A |   | 3/1987  | Landis et al. |
| 5,623,920 | A |   | 4/1997  | Bryant |
| 5,669,376 | A | * | 9/1997  | Sioutas .................. 128/200.23 |
| 5,772,085 | A |   | 6/1998  | Bryant et al. |
| 6,155,251 | A | * | 12/2000 | Hauser .................. 128/200.23 |
| 6,681,763 | B2| * | 1/2004  | Ferris .................... 128/200.23 |
| 6,737,044 | B1| * | 5/2004  | Dickinson et al. ............. 424/46 |

FOREIGN PATENT DOCUMENTS

| EP | 0 476 991 A1 | 3/1992 |
| EP | 1 008 361    | 6/2000 |
| FR | 2 732 883    | 10/1996 |
| WO | WO 00/29054  | 5/2000 |

\* cited by examiner

Primary Examiner—Steven O Douglas

(57) ABSTRACT

An adaptor for use with a container equipped with a dispensing valve that comprises a valve stem movable between an inner closed or priming position and an outer dispensing position, for dispensing doses of pressurized aerosol formulation as well as dispensers comprising such an adaptor and container; said adaptor being adapted to receive the container and comprising an actuation mechanism, said actuation mechanism being arranged such that the user will operate the mechanism by applying a depressive or squeezing force and the dose will be dispensed upon said depressive or squeezing force and said actuation mechanism being arranged such that upon release of the mechanism by the user, the valve stem of the dispensing valve will be moved automatically into its inner closed or priming position.

16 Claims, 3 Drawing Sheets

AEROSOL DISPENSERS AND ADAPTORS THEREFOR

FIELD OF THE INVENTION

This invention relates to adaptors for use in dispensers as well as to dispensers for dispensing doses of pressurized aerosol formulation, in particular for dispensing metered doses of medicament for administration to the respiratory system of a patient.

BACKGROUND OF THE INVENTION

The use of pharmaceutical aerosols and pressurized medicinal dispensers for inhalation administration of medicaments to a patient is commonplace and becoming increasingly even more important.

The medicament is generally formulated with one or more propellants (e.g. chlorofluorocarbons and more recently hydrogen-containing fluorocarbons, including hydrofluoroalkanes, such as propellant 134a ($CF_3CH_2F$) and propellant 227 ($CF_3CHFCF_3$), as well as any additional excipients or components, and then charged in a container or vial.

The container is typically fitted by means of a ferrule with a dispensing valve, in particular a metered dose dispensing valve, comprising an elongate outlet member or valve stem movable between closed and dispensing positions, to provide a dispensing canister. The dispensing canister is typically used in conjunction with an adaptor, typically having a patient port, for example a mouthpiece or a port adapted for nasal use. In conventional dispensers, such as a conventional press-and-breathe inhaler, the adaptor typically comprises a support block having a socket adapted to receive the valve stem of the dispensing valve and an orifice having open communication with the socket and the patient port.

With conventional dispensing valves, the valve stem is typically biased to its closed position with the valve stem extending outwardly relative to the container (an "outer" closed position) and to actuate or fire the valve, the valve stem is depressed inwardly to the dispensing position (an "inner" dispensing position) allowing a dose to be dispensed. For example, with a conventional press-and-breathe device, the patient fires the device by depressing the container towards the support block of the adaptor and thus depressing the valve stem inwardly, while inhaling.

Some dispensing valves, for example certain embodiments of shuttle-type metered dose dispensing valves disclosed in U.S. Pat. No. 5,772,085, do not operate in the conventional push-to-fire manner. Instead the valve stem moves relative to the container from an inner closed or priming position to an outer dispensing position. In other words, the dispensing valve is actuated or fired upon movement of the valve stem outwardly relative to the container. The operation of such valves would typically require the user to depress the valve stem inwardly to the priming position and then release to allow firing during the release stroke upon the outward movement of the valve stem to the dispensing position.

SUMMARY OF THE INVENTION

It has been recognized that the unfamiliar firing upon release (release-to-fire operation) may cause confusion for the patient. In particular, it has been appreciated that the patient often has undergone intensive training to learn how to coordinate inhaling while operating a conventional press-and-breathe type of inhaler (i.e. a push-to-fire dispenser), and thus may find it difficult, if not nearly impossible, to switch to using a dispenser based on a release-to-fire operation. This holds particularly true, because patients, such as asthma patients, often tend to be sensitive to and reluctant towards any change in the medicinal dispenser (or inhaler) they are using.

Surprisingly we have been able to provide adaptors as well as dispensers, which allow the patient to use release-to-fire-type valves in the conventional manner.

Accordingly in one aspect of the present invention there is a provided an adaptor for use with a container equipped with a dispensing valve that comprises a valve stem movable between an inner closed or priming position and an outer dispensing position, for dispensing doses of pressurized aerosol formulation, the adaptor being adapted to receive the container and comprising an actuation mechanism, said actuation mechanism being arranged such that the user will operate the mechanism by applying a depressive or squeezing force and the dose will be dispensed upon said depressive or squeezing force and said actuation mechanism being arranged such that upon release of the mechanism by the user, the valve stem of the dispensing valve will be moved automatically to its closed or priming position.

In another aspect of the present invention there is provided a dispenser for dispensing doses of pressurized aerosol formulation, said dispenser comprising:

a container containing pressurized aerosol formulation and equipped with a dispensing valve that comprises a valve stem movable between an inner closed or priming position and an outer dispensing position, to dispense a dose; and an adaptor adapted to receive the container and comprising an actuation mechanism, said actuation mechanism being arranged such that the user operates the mechanism by applying a depressive or squeezing force and the dose is dispensed upon said depressive or squeezing force and said actuation mechanism being arranged such that upon release of the mechanism by the user, the valve stem of the dispensing valve is moved automatically to its closed or priming position.

The use of adaptors or dispensers in accordance with the invention is advantageous in that the patient can operate the dispenser in a similar manner to a conventional press-and-breathe type inhaler. While inhaling, the patient exerts a depressing force upon the actuation mechanism to allow a dose to dispense. After such firing, the patient simply releases the actuation mechanism. Because the actuation mechanism is arranged such that the valve stem of the dispensing valve is moved or returned automatically to its inner closed or priming position upon said release, the dispenser is advantageously ready for the next firing without any additional operation by the patient. Dispensers in accordance with the invention are also advantageous in that due to the automatic immediate resetting of the valve to its inner closed or priming position upon release, by the patient, potentially sensitive portions of the interior of the dispensing valve are desirably sealed off from the outside environment, and thus protected from air and moisture ingress between individual firings of the dispenser.

In preferred embodiments, the actuation mechanism is arranged, such that upon said depressive or squeezing force the valve stem is pulled from its closed or priming position into its dispensing position. Such preferred embodiments are particularly advantageous for use with dispensing valves free of an internal spring bias for biasing the valve stem towards its outer dispensing position.

Suitable dispensing valves include in particular dispensing valves arranged to be of neutral bias (i.e. the valve stem being neither biased towards its closed/priming or dispensing position) as well as dispensing valves arranged, such that the valve stem will be biased outwardly towards its dispensing position by vapor pressure generated by pressurized aerosol formulation contained within the container of the dispenser.

In one embodiment, the actuation mechanism comprises a mounting block and an actuating member; said mounting block being adapted to retain the container and to prevent movement of the container relative to the adaptor and said actuating member being in contact with the valve stem and biased towards the container, such that the valve stem rests in its closed or priming position. Suitably the actuating member may be arranged, such that upon said depressive or squeezing force the actuating member moves away from the container against the bias allowing the valve stem to move into its dispensing position. Alternatively and more desirably, the actuating member may be coupled to the valve stem and arranged, such that upon said depressive or squeezing force the actuating member moves away from the container against the bias, thereby pulling the valve stem into its dispensing position.

In other embodiments, the actuation mechanism may comprise an anchoring block, which is adapted to retain the valve stem and to prevent movement of the valve stem relative to the adaptor. Here the container is desirably biased towards the valve stem, such that the valve stem rests in its closed or priming position, and the actuation mechanism desirably comprises an actuating member being arranged, such that upon said depressive or squeezing force, the actuating member moves the container against the bias away from the valve stem, thereby pulling the valve stem into its dispensing position relative to the container.

These adaptors and dispensers are particularly suitable for use with metered dose dispensing valves, more particularly shuttle-type metered dose dispensing valves. In preferred embodiments, the dispensing valve further comprises a chamber and an outlet passage, wherein the valve stem extends into the chamber and is movable relative to the chamber between the closed or priming position and the dispensing position; the valve stem having a configuration including an external surface and the chamber having an internal configuration including an internal surface, such that a movable metered volume of pressurized aerosol formulation is capable of being defined therebetween and such that during movement between the closed or priming position and the dispensing position the valve stem sequentially:

(i) allows free flow of aerosol formulation into and out of the chamber, (ii) defines a closed metered volume for pressurized aerosol formulation between the external surface of the valve stem and internal surface of the chamber, and (iii) moves with the closed metered volume within the chamber without decreasing the volume of the closed metered volume until the metered volume communicates with the outlet passage thereby allowing dispensing of the metered volume of pressurized aerosol formulation.

Further embodiments of the invention are defined in the dependent claims.

The invention, its embodiments and further advantages will be described in the following with reference to the following drawings.

DETAILED DESCRIPTION

It is to be understood that the present invention covers all combinations of particular and preferred aspects of the invention described herein.

For a better understanding of the various aspects of the present invention, one exemplary dispensing valve, which is actuated or fired upon movement of the valve stem outwardly and particularly suitable for use in the present invention, will be initially described.

Figure 1A:
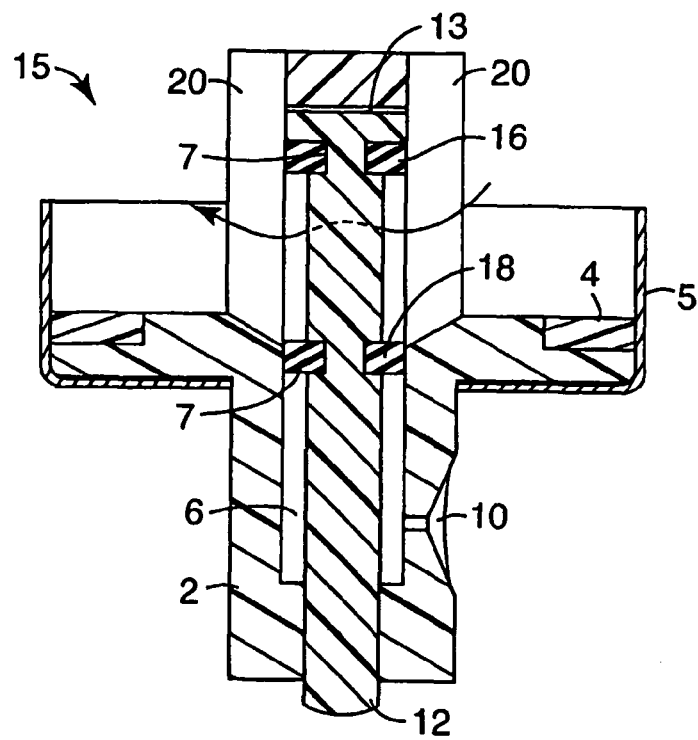
FIGS. 1a and b represent vertical cross sections through a valve comprising an valve stem movable from an inner closed or priming position to an outer dispensing position.
Figure 1B:
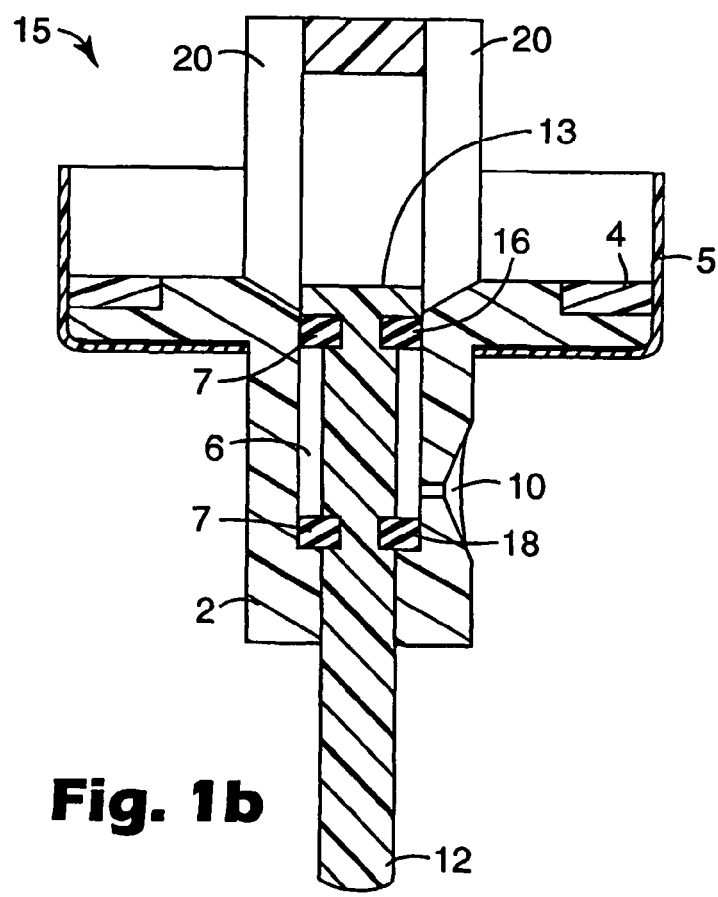

FIGS. 1a and b illustrate an exemplary shuttle-type metered dose dispensing valve. Referring to FIGS. 1a and b, the valve typically comprises a body (2) having an annular seal or gasket (4) for engaging the neck of an aerosol container or vial (not shown) to facilitate a gas-tight seal. The body (2) may be secured to the aerosol container or vial by any suitable means e.g. a conventional outer casing or ferrule (5), which is crimped around the neck of the aerosol container. As can be best seen in FIG. 1b, the body (2) defines a chamber (6) having an outlet passage (10) for dispensing e.g. pressurized aerosol formulation. The valve stem (12) extends through the chamber (6) and is movable between a closed or priming position (as shown in FIG. 1a) and a dispensing position (as shown in FIG. 1b). The valve stem (12) is desirably fitted with an inner seal (16) and outer seal (18), which provide gas-tight seals between the valve stem and the inner wall of the chamber (6). The chamber (6), external dimensions of the valve stem (12) and the positions of the seals (16 and 18) are arranged to define a pre-determined volume within the chamber (6) between the seals (16 and 18). This can be best understood by reference to FIG. 1b showing the valve in its dispensing position. As can be seen in FIG. 1a, in its closed or priming position the space between the seals (16 and 18) around the valve stem (12) extends into the reservoir containing aerosol formulation. As the valve stem (12) moves downwardly to its dispensing position, the seal (18) moves down the chamber allowing free access of the aerosol formulation in to the chamber (6). Further movement of the valve stem causes seal (16) to enter the chamber (6) thereby trapping a metered volume of aerosol formulation between the seals (16 and 18) and the interior wall of the chamber (6). When the valve stem reaches its dispensing position the seal (18) passes outlet passage (10) thereby allowing direct communication between the metered volume and the outlet passage (10) thereby allowing the metered volume of formulation to be dispensed. In the illustrated valve, the valve is arranged, in particular the cross-sectional area of the seals (16 and 18) is arranged, such that the valve stem will be biased outwardly towards its dispensing position by vapor pressure generated by pressurized aerosol formulation contained within the container of the dispenser. The alignment of the valve stem may be ensured by ribs (20) which do not obstruct the free flow of aerosol formulation (as depicted by the arrow in FIG. 1a) around the valve stem (12) between the seals (16 and 18).

It is to be understood that FIGS. 1a and b show one exemplary dispensing valve, which is suitable for use in the present invention, and that other dispensing valves, in particular other metered dose dispensing valves, having a valve stem movable between an inner closed or priming position and an outer dispensing position may also be suitable for use. Further examples of dispensing valves, which are actuated or fired upon movement of the elongate outlet member or valve stem outwardly, are described in U.S. Pat. No. 5,772,085, the contents of which are incorporated herein by reference. Other examples of dispensing valves, which are actuated or fired upon movement of an elongate outlet member or valve stem are described in U.S. Pat. Nos. 2,980,301; 3,176,887; 3,176,889; 3,591,059; and 4,506,803.

Figure 2:
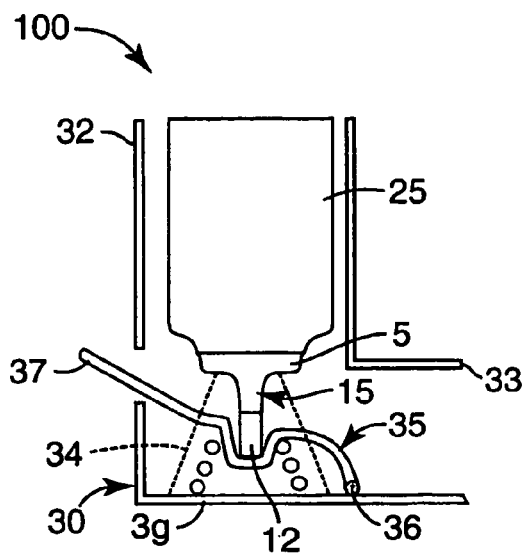
FIG. 2 represents schematically a vertical cross section of a preferred embodiment of the dispenser in accordance with the invention.

FIG. 2 shows schematically a vertical cross-section of a preferred embodiment of a dispenser (100) in the form of an inhaler incorporating a preferred embodiment of an adaptor (30). The adaptor comprises an elongate or cylindrical portion (32), adapted to received the aerosol container (25) equipped with a dispensing valve (generally indicated at 15) comprising a valve stem (12) movable between an inner closed or priming position and an outer dispensing position. The dispensing valve is typically fitted onto the container by means of a ferrule (5) with the valve stem extending beyond the ferrule. The adaptor also typically comprises a mouthpiece portion (33). A mounting block (34) is provided that supports and retains the container (25), in particular at the position of the ferrule (5), preventing movement of the container. The mounting block (34) is desirably arranged, such that the outlet passage (not shown) of the dispensing valve is aligned along the axis of the mouthpiece portion (33). The adaptor includes an actuation member (35) provided in the form of a lever, which is mounted on a pivot (36) and has a user end (37), which extends externally from the adaptor, in particular from the elongate or cylindrical portion (32) of the adaptor. The actuating member (35) is biased upwardly towards the container (25) by the action of a conical compression spring (39) mounted between the actuating member and an internal surface of the adaptor. The outer end of the valve stem (12) rests against the actuating member (35), and because the member is biased upwardly towards the container, the valve stem normally rests in its closed or priming position.

In operation, the patient presses downwards on the user end (37) of the actuating member (35), whilst simultaneously inhaling through the mouthpiece portion (33). In so doing, the patient causes the actuating member (35) to pivot downwards against the action of the spring (39), thereby allowing the valve stem (12) to move outwardly into its dispensing position.

Desirably the dispensing valve is arranged, such that the valve stem is biased outwardly towards its dispensing position by vapor pressure generated by pressurized aerosol formulation contained within the container of the dispenser. Thus, the valve stem moves outwardly into its dispensing position under the influence of the internal vapor pressure. Alternatively, the dispensing valve may include an internal spring bias positioned at the inner end of the valve stem (not shown) biasing the valve stem towards its dispensing position. In this case, the valve stem moves outwardly into its dispensing position under the influence of the internal spring bias.

After taking a dose of medicament, the patient simply releases the actuating member (35), allowing the spring (39) to return the actuating member to its rest position and thus the valve stem (12) into its closed or priming position. This reset action occurs automatically as soon as the patient releases the actuating member (35), thereby minimizing the time in which internal portions of the dispensing valve, such as a virtual metering chamber, may be open to air or atmospheric moisture. It will be appreciated that in embodiments including a dispensing valve comprising an internal spring bias, the spring of the adaptor will be selected to exert, over the range of spring extensions corresponding to the return of the valve stem from its outer dispensing position to its closed or priming position, a suitably greater compressive force that that exerted by the internal spring.

Figure 3:
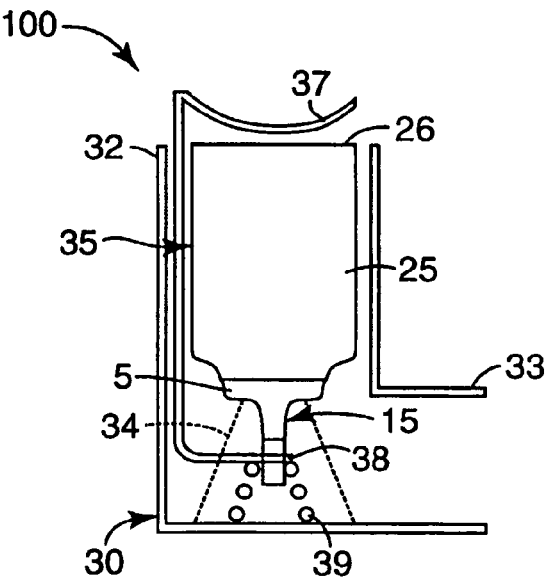
FIG. 3 represents schematically a vertical cross section of another preferred embodiment of the dispenser in accordance with the invention.

FIG. 3 shows schematically a vertical cross-section of another preferred embodiment of a dispenser (100) in the form of an inhaler incorporating another preferred embodiment of an adaptor (30). Similar to the dispenser illustrated in FIG. 2, the adaptor comprises an elongate or cylindrical portion (32), adapted to received the aerosol container (25) equipped with a dispensing valve (generally indicated at 15) comprising a valve stem (12) movable between an inner closed or priming position and an outer dispensing position. The adaptor also includes a mouthpiece portion (33) as well as a mounting block (34) that supports and retains the container, in particular at the position of the ferrule (5), preventing movement of the container. The adaptor includes an actuating member (35) in the form of a slider. The actuating member (35), which in its cross-section is essentially C-shaped, is located within a gap between the elongate or cylindrical portion (32) and the container (25), with a user end (37) extending outwardly from the open end of the elongate or cylindrical portion (32) and the other end, the internal end, (38) gripping the valve stem. The user end (37) of the actuating member is preferably provided in the form of a concave recess extending over the closed end (26) of the container. A conical compression spring (39) is mounted between the internal end of the actuating member (35) and an internal surface of the adaptor, such that the actuating member is biased upwardly towards the container, so that the valve stem (12) normally rests in its closed or priming position.

In operation, the patient depresses the user end (37) of the actuating member (35), typically by placing their finger(s) in the concave recess of the user end, whilst simultaneously inhaling through the mouthpiece portion (33). In so doing, the patient causes the actuating member (35) to move downwards against the action of the spring (39), thereby pulling the valve stem (12) into its dispensing position.

The arrangement of the actuation mechanism, such that upon a depressive or squeezing force applied by the user the valve stem is pulled into its dispensing position (referred to as "positive pull out action" in the following) is advantageous in that it guarantees the provision of enough force to move the valve stem (12) without the need for an internal spring bias within the dispensing valve. Thus, potential problems associated with the immersion of a spring in a medicinal aerosol formulation can be avoided. Such potential problems may include for example medicament deposition on the large and flexing surface area of the spring, chemical interactions between the drug and the spring, and hindrance to the free flow of aerosol formulation into and out of the chamber. This embodiment and other embodiments (e.g. as described below) including positive pull-out action are particularly desirable for use with dispensing valves having neutral bias or dispensing valves in which the valve stem is biased towards its dispensing position only by vapor pressure generated by the pressurized aerosol formulation contained in the container.

After taking a dose of medicament, the patient simply releases the actuating member (35), allowing the spring (39) to automatically return the actuating member to its rest position and thus the valve stem (12) to its inner closed or priming position.

Figure 4:
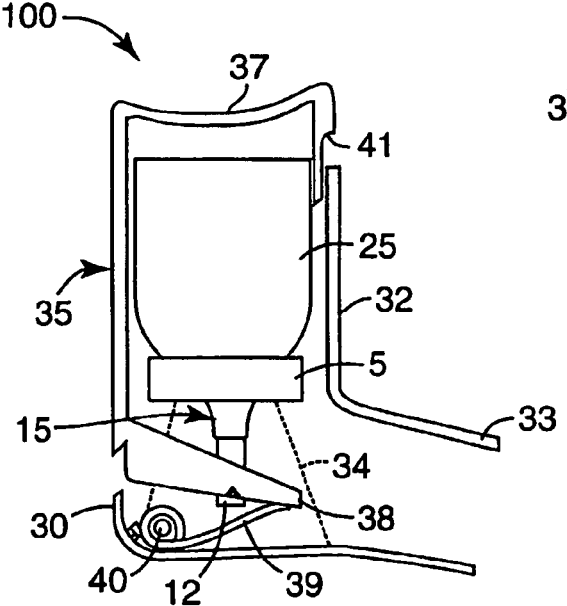
FIG. 4 represents schematically a vertical cross section of an additional preferred embodiment of the dispenser in accordance with the invention.

FIG. 4 shows schematically a vertical cross-section of a variation of the preferred embodiment of the dispenser (100) shown in FIG. 3. This dispenser is generally similar to the dispenser illustrated in FIG. 3, except that the spring (39) is in the form of a torsion spring mounted via a post (40) on the adaptor (30). The user end (37) of the actuating member (35) additionally comprises a movement stop (41), which will act against the top rim of the elongate or cylindrical portion (32) of the adaptor (30). This stop (41) desirably limits and defines the maximum stem movement possible. The other end of the actuating member (35), the internal end (38), is fixedly located on the valve stem (12). The principles of operation are analogous with those described in conjunction with the dispenser shown in FIG. 3.

Figure 5:
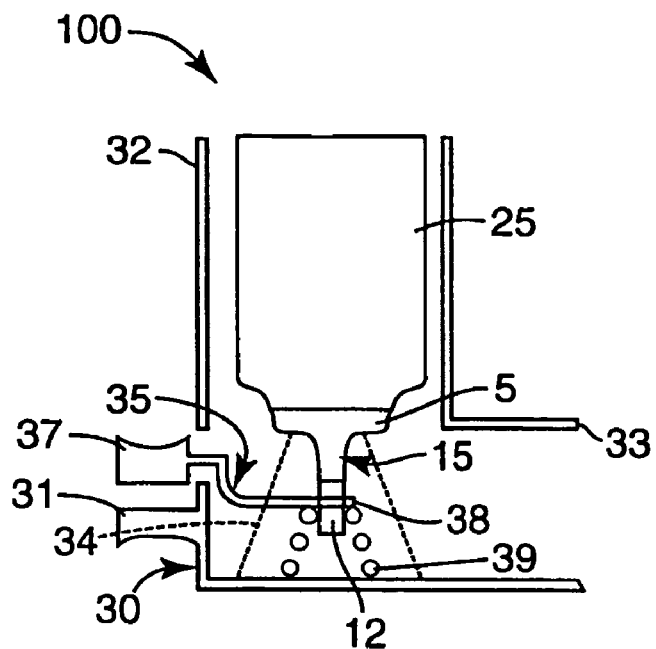
FIG. 5 represents schematically a vertical cross section of a further preferred embodiment of the dispenser in accordance with the invention.

FIG. 5 shows schematically a vertical cross-section of an additional preferred embodiment of a dispenser (100) in the form of an inhaler incorporating an additional preferred embodiment of an adaptor (30). This dispenser is similar to the dispenser illustrated in FIG. 3, with an exception that the actuating member (35) has a different shape. In particular, the user end (37) of the actuating member, which is desirably in the form of a finger-button, extends outwardly from a side wall of the of the adaptor, in particular the elongate or cylindrical portion (32) thereof. In addition, an extension (31), also desirably in the form of a finger-bottom, is provided on an external surface of the adaptor in a corresponding position to allow its use in coordination with the user end (37) of the actuating member (35). The patient operates the actuation mechanism by squeezing together the user end (37) of the actuating member (35) and the extension (31). The principles of operation are analogous with those described in conjunction with the dispenser shown in FIG. 3.

Figure 6:
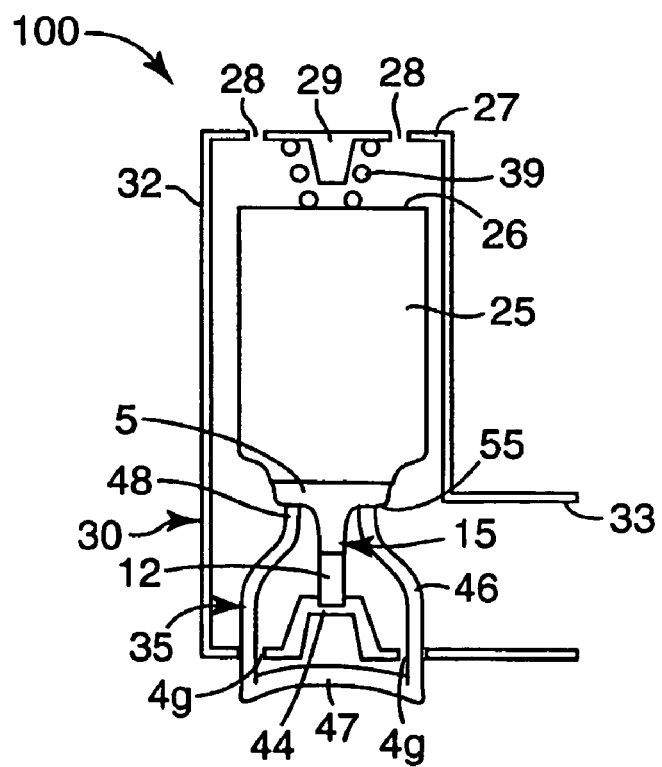
FIG. 6 represents schematically a vertical cross section of a yet further preferred embodiment of the dispenser in accordance with the invention.

FIG. 6 shows schematically a vertical cross-section of a further preferred embodiment of a dispenser (100) in the form of an inhaler incorporating a further preferred embodiment of an adaptor (30). Similar to the other embodiments illustrated in FIGS. 2 to 5, the adaptor (30) comprises an elongate or cylindrical portion (32), adapted to receive the aerosol container (25) equipped typically by means of a ferrule (5) with a dispensing valve (generally indicated at 15) comprising a valve stem (12) movable between an inner closed or priming position and an outer dispensing position. In this embodiment, the adaptor is provided with an anchoring block (44), which retains the outer end of the valve stem (12) and prevents movement of the valve stem relative to the adaptor. The anchoring block (44) is desirably arranged, such that the outlet orifice (not shown) of the dispensing valve is aligned along the axis of the mouthpiece portion (33). The elongate or cylindrical portion (32) of adaptor includes an end-cap (27) over the closed end (26) of the container (25). For airflow, orifices (28) may be provided in the end-cap as shown or alternatively in the adaptor near the anchoring block. A conical compression spring (39) is mounted on a guide post (29) between an internal surface of the end-cap (27) and an outer surface of the closed end (26) of the container, such that the container is biased downwardly towards the valve stem, so that the valve stem (12) normally rests in its inner closed or priming position. The adaptor includes an actuating member (35), which is essentially U-shaped in its cross-section. The actuating member is mounted, such that the base portion (47) of the member is located adjacent to an external surface of the adaptor and the side wall or side fingers (46) extend(s) into the interior of the adaptor. The upper edge (48) of the side wall or side fingers is adjacent to the underside of the container (25), in particular the underside of the shoulder (55) of the ferrule (5). The base portion (47), which serves as a user portion of the actuating member, is desirably in the form of a concave recess or thumb-button. For ease in inserting the side wall or side fingers (46) through appropriate slots (49) in the adaptor body, the side wall or fingers (46) may be flexible. The side wall or side fingers (46) may be provided with projections (not shown) to prevent the removal or detachment of the actuating member (35) from the adaptor body by the patient.

In operation, the patient presses the base portion (47) of the actuating member (35) towards the adaptor body, whilst simultaneously inhaling through the mouthpiece portion (33). In so doing, the patient causes the actuating member (35) to push the container (25) upwardly against the action of the spring (39), thereby pulling (in a relative movement) the valve stem (12) into its dispensing position. After taking a dose of medicament, the patient simply releases the base portion (47) of the actuating member (35), allowing the spring (39) to automatically return the container (25) to its rest position and thus the valve stem (12) in its inner closed or priming position.

It will be understood that the present disclosure of particular preferred embodiments in accordance with the invention is for the purpose of illustration only and the invention extends to modifications, variations and improvements thereof.

The invention claimed is:

1. An adaptor for use with a container equipped with a dispensing valve that comprises a valve stem movable between an inner closed or priming position and an outer dispensing position, for dispensing doses of pressurized aerosol formulation, the adaptor being adapted to receive the container and comprising an actuation mechanism, said actuation mechanism being arranged such that the user will operate the mechanism by applying a depressive or squeezing force and the dose will be dispensed upon said depressive or squeezing force and said actuation mechanism being arranged such that upon release of the mechanism by the user, the valve stem of the dispensing valve will be moved automatically into its closed or priming position.

2. An adaptor according to claim 1, wherein the actuation mechanism is arranged, such that upon said depressive or squeezing force the valve stem will be pulled from its closed or priming position into its dispensing position.

3. An adaptor according to claim 1, wherein the actuation mechanism comprises a mounting block and an actuating member; said mounting block being adapted to retain the container and to prevent movement of the container relative to the adaptor and said actuating member being arranged to be in contact with the valve stem and biased towards the container, such that the valve stem will rest in its closed or priming.

4. A dispenser for dispensing doses of pressurized aerosol formulation to a user, said dispenser comprising:
a container containing a pressurized aerosol formulation and equipped with a dispensing valve that comprises a valve stem movable between an inner closed or priming position and an outer dispensing position, to dispense a dose; and
an adaptor adapted to receive the container and comprising an actuation mechanism, said actuation mechanism being arranged such that the user operates the mechanism by applying a depressive or squeezing force and the dose is dispensed upon said depressive or squeezing force and said actuation mechanism being arranged such that upon release of the mechanism by the user, the valve stem of the dispensing valve is moved automatically to its closed or priming position.

5. A dispenser according to claim 4, wherein the actuation mechanism is arranged, such that upon said depressive or squeezing force the valve stem is pulled from its closed or priming position into its dispensing position.

6. A dispenser according to claim 4, wherein the actuation mechanism comprises a mounting block and an actuating member; said mounting block being adapted to retain the container and to prevent movement of the container relative to the adaptor and said actuating member being in contact with the valve stem and biased towards the container, such that the valve stem rests in its closed or priming.

7. A dispenser according to claim 6, wherein said actuating member is arranged, such that upon said depressive or squeezing force the actuating member moves away from the container against the bias allowing the valve stem to move into its dispensing position.

8. A dispenser according to claim 5, wherein the actuation mechanism comprises an anchoring block, which is adapted to retain the valve stem and to prevent movement of the valve stem relative to the adaptor, and wherein the container is biased towards the valve stem, such that the valve stem rests in its closed or priming position, and wherein said actuation mechanism further comprises an actuating member, said actuating member being arranged, such that upon said depressive or squeezing force, the actuating member moves the container against the bias away from the valve stem, thereby pulling the valve stem into its dispensing position relative to the container.

9. A dispenser according to claim 4, wherein the dispensing valve is arranged, such that the valve stem is biased towards its dispensing position by vapor pressure generated by the pressurized aerosol formulation.

10. A dispenser according to claim 4, wherein the dispensing valve is of neutral bias.

11. A dispenser according to claim 7, wherein the dispensing valve comprises an internal spring bias positioned at the inner end of the valve stem biasing the valve stem towards its dispensing position.

12. A dispenser according to claim 4, wherein the dispensing valve is a metered dose dispensing valve.

13. A dispenser according to claim 12, wherein the dispensing valve further comprises a chamber and an outlet passage, and the valve stem extends into the chamber and is movable relative to the chamber between the closed or priming position and the dispensing position, the valve stem having a configuration including an external surface and the chamber having an internal configuration including an internal surface, such that a movable metered volume of pressurized aerosol formulation is capable of being defined there between and such that during movement between the closed or priming position and the dispensing position the valve stem sequentially:

(i) allows free flow of aerosol formulation into and out of the chamber, (ii) defines a closed metered volume for pressurized aerosol formulation between the external surface of the valve stem and internal surface of the chamber, and (iii) moves with the closed metered volume within the chamber without decreasing the volume of the closed metered volume until the metered volume communicates with the outlet passage thereby allowing dispensing of the metered volume of pressurized aerosol formulation.

14. A dispenser according to claim 4, wherein the pressurized aerosol formulation comprises medicament.

15. A dispenser according to claim 4, wherein the pressurized aerosol formulation comprises a propellant selected from HFA 134a, HFA 227 and mixtures thereof.

16. A dispenser according to claim 4, wherein the dispenser is in the form of an inhaler.

* * * * *